United States Patent
Ramsbottom et al.

(10) Patent No.: US 7,197,781 B2
(45) Date of Patent: Apr. 3, 2007

(54) NECK SUPPORT

(76) Inventors: John E. Ramsbottom, 2019 Atkinson Drive, Burlington, Ontario (CA) L7M 4J1; Damon G. Racicot, 129 King Street West, Ingersoll, Ontario (CA) N5C 2J7

( * ) Notice: Subject to any disclaimer, the term of this patent is extended or adjusted under 35 U.S.C. 154(b) by 78 days.

(21) Appl. No.: 10/979,217

(22) Filed: Nov. 3, 2004

(65) Prior Publication Data

US 2005/0102758 A1 May 19, 2005

Related U.S. Application Data

(60) Provisional application No. 60/517,085, filed on Nov. 5, 2003.

(51) Int. Cl.
*A47G 9/10* (2006.01)
(52) U.S. Cl. .............................. 5/636; 5/640
(58) Field of Classification Search .................. 5/636, 5/640, 637; 297/393
See application file for complete search history.

(56) References Cited

U.S. PATENT DOCUMENTS

| | | | | |
|---|---|---|---|---|
| 98,859 A * | 1/1870 | Fast | ............................ | 297/393 |
| 673,872 A * | 5/1901 | von Hillern-Flinsch | ..... | 297/391 |
| 1,510,187 A * | 9/1924 | Martin | ........................ | 297/393 |
| 4,218,792 A * | 8/1980 | Kogan | ........................... | 5/636 |
| 4,345,347 A * | 8/1982 | Kantor | .......................... | 5/644 |
| 4,550,458 A * | 11/1985 | Fiore | ............................. | 5/637 |
| 4,617,691 A * | 10/1986 | Monti et al. | .................... | 5/640 |
| 4,738,488 A * | 4/1988 | Camelio | ...................... | 297/383 |
| 4,776,049 A * | 10/1988 | Perron | ............................ | 5/640 |
| 5,220,700 A * | 6/1993 | Liu | ................................. | 5/636 |
| 5,339,472 A * | 8/1994 | Yin | ................................ | 5/636 |
| 5,441,479 A * | 8/1995 | Chitwood | .................... | 602/18 |
| 5,454,781 A * | 10/1995 | Chitwood | .................... | 602/18 |
| 5,483,698 A * | 1/1996 | Douglas, Jr. | ................... | 2/462 |
| 5,551,081 A * | 9/1996 | Starnes et al. | ................. | 2/468 |
| 5,916,185 A * | 6/1999 | Chitwood | .................... | 602/18 |
| 6,006,381 A * | 12/1999 | Tandrup | ......................... | 5/655 |
| 6,009,566 A * | 1/2000 | Hubbard | ......................... | 2/468 |
| 6,216,298 B1 * | 4/2001 | Oliveira | ......................... | 5/636 |
| 6,308,345 B1 | 10/2001 | Williams, Jr. | | |
| 6,447,468 B1 * | 9/2002 | Hankins et al. | ............... | 602/18 |
| 6,622,727 B2 * | 9/2003 | Perry | .......................... | 128/845 |
| 6,742,207 B1 * | 6/2004 | Brown | .......................... | 5/636 |
| 6,859,965 B1 * | 3/2005 | Gourd | ............................ | 5/646 |
| 6,895,619 B1 * | 5/2005 | Lee | ................................. | 5/636 |
| 7,017,194 B2 * | 3/2006 | Schroth | ......................... | 2/410 |
| 7,082,633 B1 * | 8/2006 | Maarbjerg | ...................... | 5/636 |
| 2005/0076442 A1 * | 4/2005 | Wassilefky | .................... | 5/636 |
| 2005/0102757 A1 * | 5/2005 | Lee | ................................. | 5/636 |
| 2005/0102758 A1 * | 5/2005 | Ramsbottom et al. | .......... | 5/636 |
| 2005/0278852 A1 * | 12/2005 | Wahrmund et al. | ............ | 5/636 |
| 2006/0174414 A1 * | 8/2006 | Maarbjerg | ...................... | 5/636 |

* cited by examiner

*Primary Examiner*—Robert G. Santos
(74) *Attorney, Agent, or Firm*—Jeffrey W. Wong; Borden Ladner Gervais LLP

(57) ABSTRACT

The present invention is directed at a neck support comprising a top portion for receiving a user's head; a bottom portion having a pair of wings for resting on shoulders of said user; a middle portion, connecting said top potion to said bottom portion; said top and middle portions are made of a compressive mould material having memory characteristics.

5 Claims, 6 Drawing Sheets

NECK SUPPORT

CROSS REFERENCE TO RELATED APPLICATIONS

This application claims the benefit of U.S. Provisional Application No. 60/517,085, filed Nov. 5, 2003, which is incorporated herein by reference.

FIELD OF THE INVENTION

The present invention relates generally to orthopaedic supports. More particularly, the present invention relates to a neck support.

BACKGROUND OF THE INVENTION

Neck injuries are becoming more and more prevalent in society. Some of these injuries are due to workers having to subject their neck to a reclined position for an extended period of time. Since necks are a very complex structure this abuse results in users having short term problems such as a stiff neck or even medium to longer term concerns. Some examples include painters, electricians, construction or utility workers who are constantly looking up during their work day.

There are various solutions to alleviating the stress which is placed on the user's neck during these situations, however, simple supports or static rests cause the user's neck muscles to shut down and/or weaken, creating short-term benefits but with medium and long term concerns. Also when a static fixed rest is employed, the user does not gain any benefit until the full extension of the rest is being contacted by the user's neck. From that point, if any further extension is required, the user redirects their bending motion to the lower back where a greater risk for injury exists. Additionally, with solid static rests that support the neck on the cervical discs, these supports act as a fulcrum that may cause severe injury should the user be struck from behind.

One example of a prior art neck support is described in US Published Patent Application No. 2003/0050582 entitled Head Support which describes a rigid member, positioned by a harness over the user's upper body, which provides support to a user's head when the head is tilted backwards so that there is support to the back of the user's head when the user is attempting to view an object above the horizontal. However, the rigidity of the rigid member does not provide relief to a user's head since it holds the head in a constant upright position which may be uncomfortable to the user.

It is, therefore, desirable to provide a neck support which overcomes some of the disadvantages of the prior art.

SUMMARY OF THE INVENTION

It is an object of the present invention to obviate or mitigate at least one disadvantage of previous neck supports.

The neck support of the present invention is manufactured out of a compressive memory material that is in immediate contact with the neck upon extension providing the user with support through the full range of motion of the neck. Full, supported range of motion is achieved without other biomechanical concerns being raised.

The neck muscles are also supported such that full inhibition of the muscles does not occur, thus reducing long-term fatigue and ultimate weakness of the muscles. The neck support is dynamic in that the compressive material does not restrict the user's neck from moving and allows the user to change the position of the neck when in use.

Furthermore, the neck support of the present invention is secured comfortably over the upper thoracic (T1) not the cervical vertebra thereby reducing potential injury if the user is struck from behind. The neck support is flexible and designed as a "one size fits all" including users who require hard hats.

In a first aspect, the present invention is directed at a neck support comprising a top portion for receiving a user's head; a bottom portion having a pair of wings for resting on shoulders of said user; a middle portion, connecting said top potion to said bottom portion; said top and middle portions are made of a compressive mould material having memory characteristics.

Other aspects and features of the present invention will become apparent to those ordinarily skilled in the art upon review of the following description of specific embodiments of the invention in conjunction with the accompanying figures.

BRIEF DESCRIPTION OF THE DRAWINGS

Embodiments of the present invention will now be described, by way of example only, with reference to the attached Figures, wherein.

DETAILED DESCRIPTION

Generally, the present invention provides a neck supporting device which provides support to a user's neck while they are working in order to prevent injuries or soreness to the user's neck.

Figure 1:
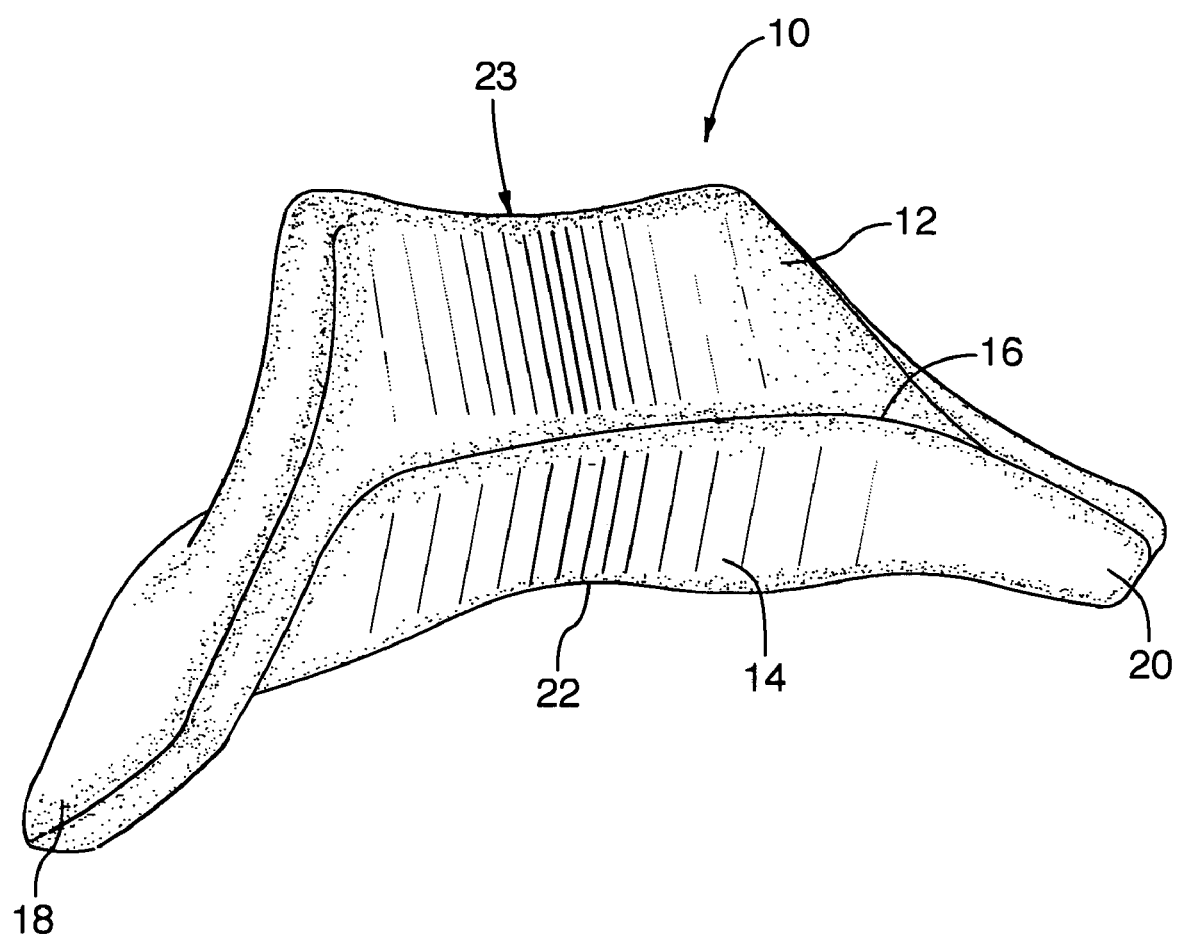
FIG. 1 is a front view of a neck support.

Turning to FIG. 1, a perspective view of a neck support 10 in accordance with the present invention is shown. The neck support 10 is preferably manufactured from a compressive mould material, such as a gel-foam polyurethane, having memory characteristics so that the neck support 10 allows a user's head to be in an extended position for sustained periods of time without a continual loading on the soft tissues and particular structures of the neck. The compressive nature of the material allows the user to move their head while working but provides continual support to the user. Furthermore, the gel-foam polyurethane has the advantage of providing biomechanical support to the neck, while extending maximum comfort, hygiene and durability.

The neck support 10 comprises a top portion 12, seen as a head surface, connected to a bottom portion 14 via a curved middle section 16. The bottom portion 14 comprises a pair of wings 18 and 20 extending outwards away from the top portion 12. As can also be seen in FIG. 1, a notch 22 is located at the centre of the bottom portion 14. In use, the notch 22 rests atop the nape of the neck of the user with the wings 18 and 20 resting on the shoulders of the user. The top of the user's neck/base of the user's head rests on the top of the top potion 12 in a pocket 23.

Figure 2:
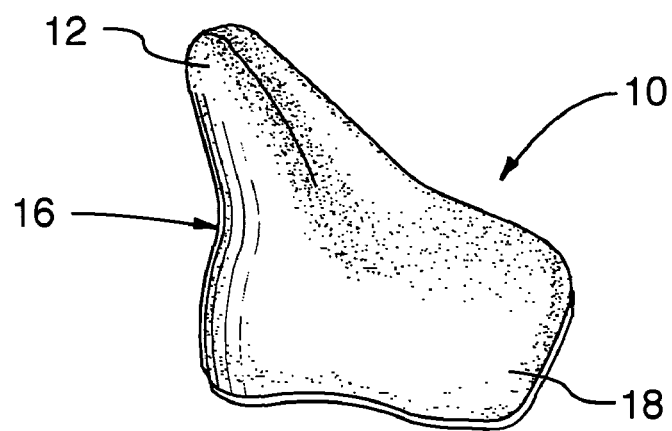
FIG. 2 is a side view of the neck support.

Turning to FIG. 2, a side view of the neck support 10 is shown. As can be seen, the neck support 10 is preferably a one-piece structure with the top portion 12 slightly angled from the vertical. The top portion 12 may be compressed along the curved middle portion 16 when the user's head contacts the pocket 23 in the top portion 12 in an alternative embodiment, the top portion 12 is substantially straight while the curved section 16 and the bottom portion 14 are approximately 135 degrees from the top portion 12.

Figure 3:
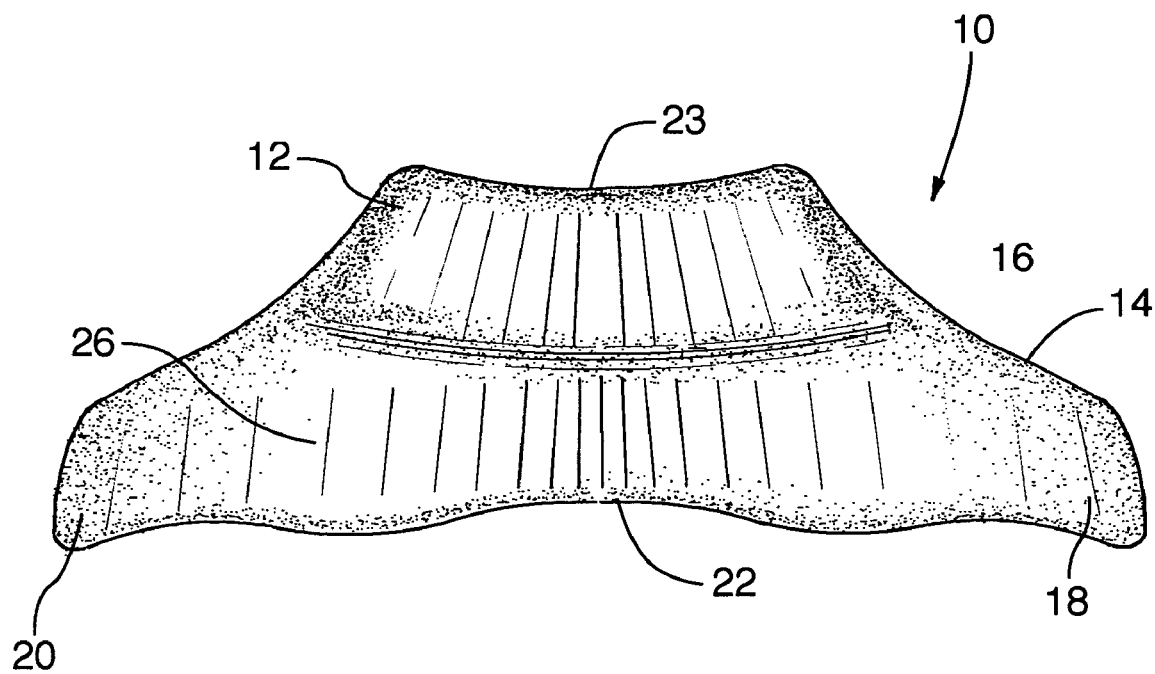
FIG. 3 is a rear view of the neck support.

Turning to FIG. 3, a rear view of the neck support 10 is shown. The respective sizes of the top portion 12, the middle portion 16 and the bottom potion 14 are more clearly shown. The respective span of the wings 18 and 20 is also shown. However, it should be noted that this is simply illustrative of one embodiment.

Figure 4:
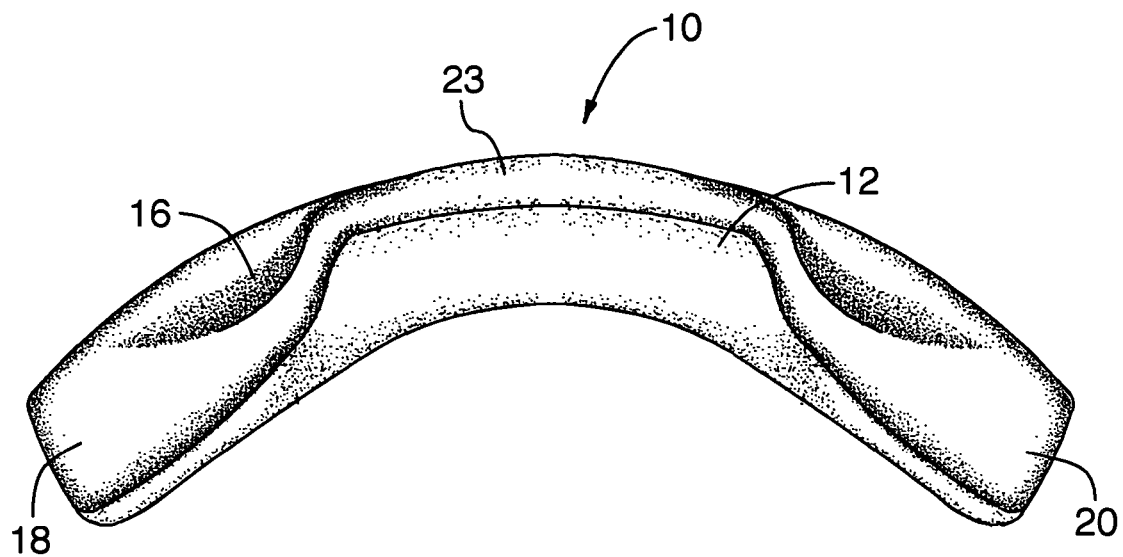
FIG. 4 is a top view of the neck support.

Turning to FIG. 4, a top view of the neck support 10 is shown. From FIG. 4, it may be seen that the curved middle portion 16 spans the width of the top potion 12 and provides a smooth transition between the top and bottom portions 12 and 14. Also, the bottom portion 14 is slightly behind the top portion 12 when viewed from the top in order to accommodate the shape of the user's head, neck and shoulders.

Figure 5:
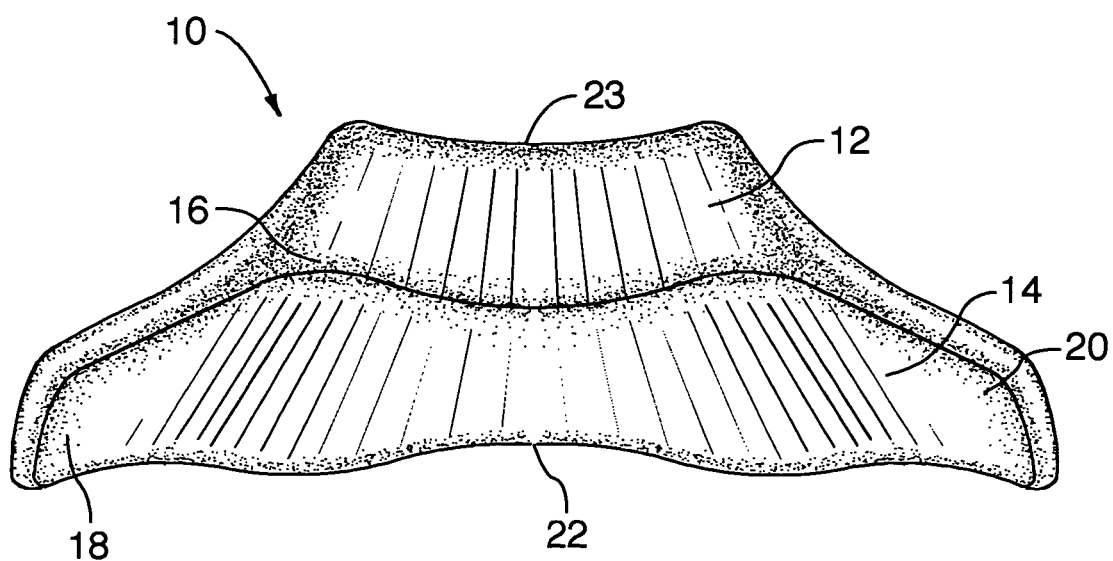
FIG. 5 is a front view of the neck support.

Turning to FIG. 5, a front view of the neck support 10 is shown. When the base of the user's head is resting against the pocket 23, the curved middle portion 16 bends in order to provide relief to the user's neck and to reduce the amount of stress which may be placed on the user's neck. Furthermore, the curvature of the support 10 is such that the support comfortably fits over the user's shoulders. The compressive material also allows the bottom portion 14 and the wings 18 and 20 to bend so that the support may accommodate various shoulder shapes and widths. The support is preferably used when a user is required to look upwards for an extended period of time such as painting or construction or utility work.

In use, the neck support 10 is centered over the user's back and positioned with the notch 22 over the upper thoracic at T1 of the user. The notch 22 provides extra comfort to the user. This causes the base of the user's head to rest in the recess and the user's neck to rest against the top portion 12 such that when the user bends their neck to look up, the neck support 10 compresses and bends along the curved middle section 16 to provide support to the user. On both sides of the bottom portion 14 the wings 18 and 20 rest over a portion of the user's shoulders. Generally, the neck support 10 is attached to a strap in which the wings 18 and 20 assist to transition the strap over the clavicle of the user, preferably anteriorly, to provide comfort and to assist in positioning the neck support over the upper thoracic. This will be described in more detail below.

When the user returns their head to the resting position (looking forward rather than up), the neck support 10 returns to its original resting position with the curved middle portion re-straightening due to the memory characteristic of the compressive mould material from which the neck support is manufactured. In this manner, others may use the neck support since the neck support returns to the original position after each use which provides an advantage over prior art neck supports.

Figure 6:
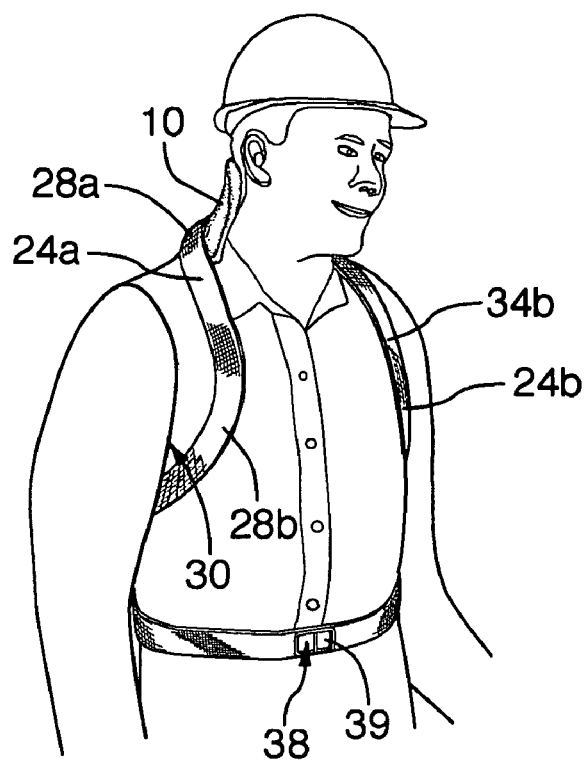
FIG. 6 is a perspective view of the neck support in use with a first strap attachment.
Figure 6A:
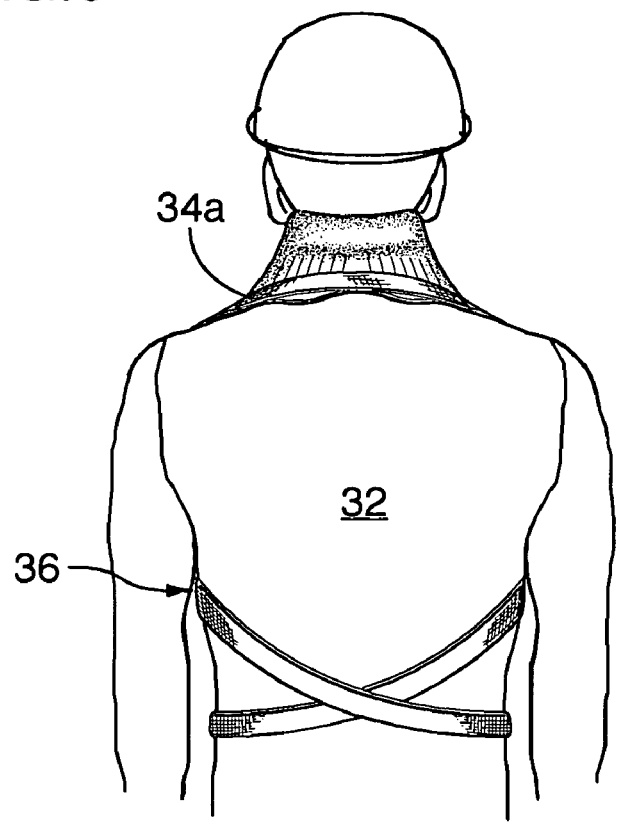
FIG. 6a is a rear view of the user in FIG. 6.

Turning to FIGS. 6 and 6a, the neck support 10 is shown in use and connected to a pair of straps 24a and 24b so that the neck support may be harnessed to the user. In general, the straps 24a and 24b are secured onto the material of the support following a relief line 26 (shown in FIG. 3) on the back of the bottom portion 14, keeping the neck support 10 low and over the upper thoracic (T1). For instance, the straps may be sewn to the bottom portion 14 of the neck support. The wings 18 and 20 of the neck support 10 rests across the upper back and shoulders of the user with the straps 24 holding the support in place.

One end 28a of the first strap 24a is connected to one of the wings 18 of the bottom portion 14 while a second end 28b of the strap 24a passes over the right clavicle of the user, through a user's right axilla, or armpit, 30 and then around the user's back 32 before being brought back around the front of the user. One end 34a of the second strap 24b is connected to the other wing 20 of the bottom portion 14 while a second end 34b of the second strap 24b passes over the user's left clavicle, through the left axilla 36 and then around the user's back 32 before being brought back around the front and then attached to the second end 28b of the first strap 24a at the front of the user using a fastening device 38 such as a clip 39.

Figure 7:
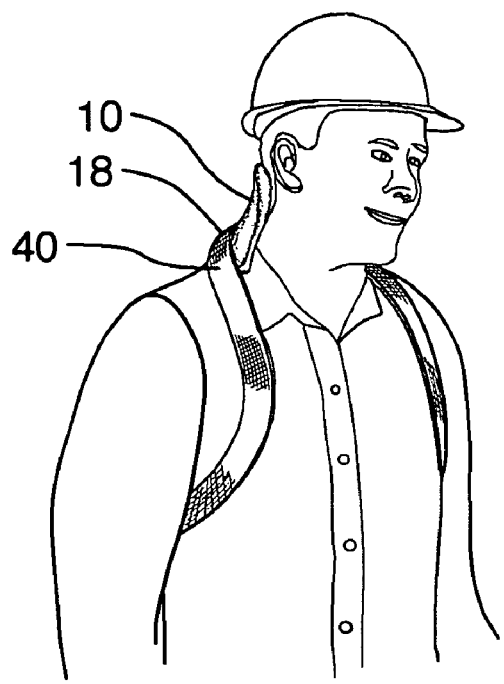
FIG. 7 is a perspective view of the neck support in use with a second strap attachment.
Figure 7A:
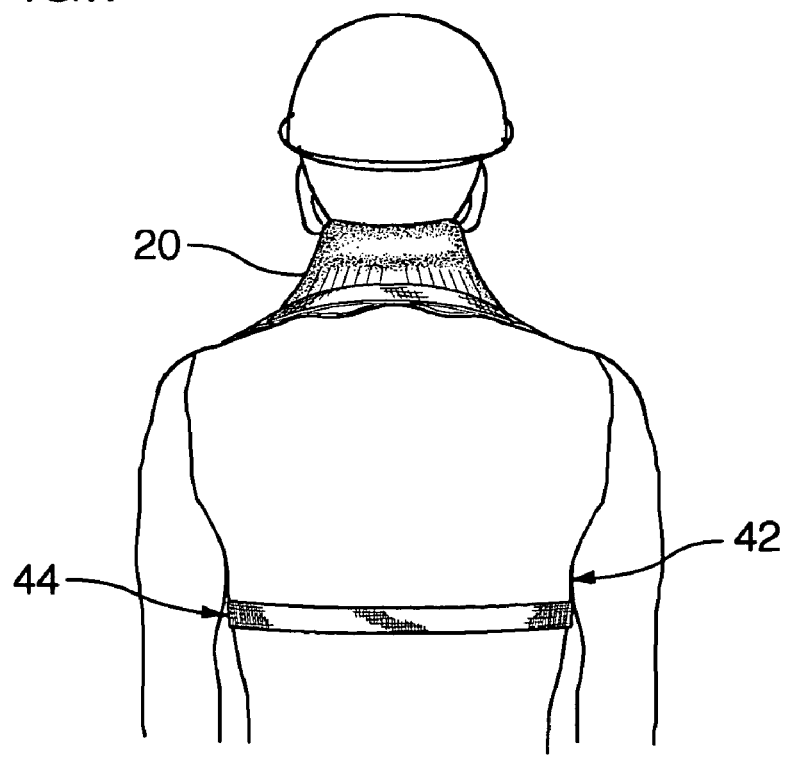
FIG. 7a is a rear view of the user in FIG. 7.

Turning to FIGS. 7 and 7a, the neck support 10 in use connected to a second embodiment of a strap is shown. In this embodiment, a strap 40 starts from one of the wings 18 and passes over the user's clavicle, through a right axilla 42 and then around the back of the user before coming back around to the front under the other axilla 44 of the user and then connected to the other wing 20. In this embodiment, a single strap is used and may be a stretchable continuous strap in order to fit multiple body types. As above, the strap 40 is attached to the relief line 26 on the back of the bottom portion 14 of the neck support 10.

Figure 8:
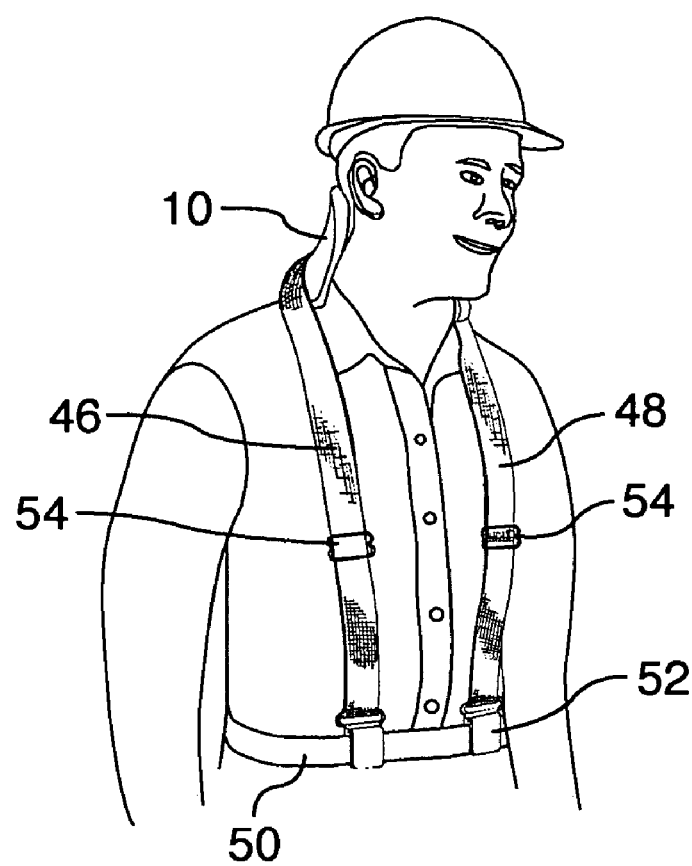
FIG. 8 is a perspective view of the neck support in use with a third strap attachment.
Figure 8A:
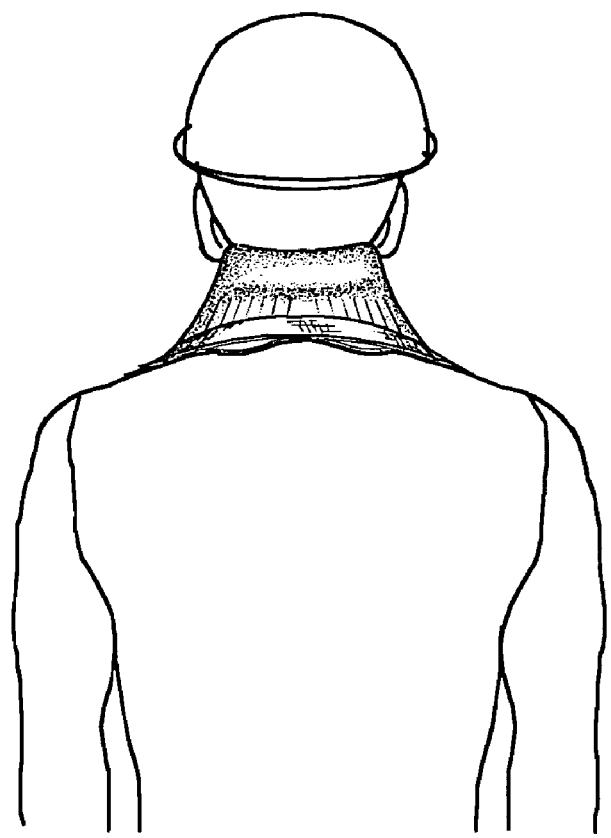
FIG. 8a is a rear view of the user in FIG. 8.

Turning to FIGS. 8 and 8a, a third embodiment of the neck support 10 in use with a third embodiment of straps is shown. In this embodiment, separate straps 46 and 48 pass from both wings 18 and 20, anteriorly to the pants or belt 50 of the user. The straps 46 and/or 48 may then be attached using fastening means 52 such as clips. Either strap 46 or 48 may comprise adjustable sliders 54 to adjust the straps to the dimensions of the user. Ends of the straps 46 and 48 are connected to the wings 18 and 20 of the support 10.

In each of the neck support and strap confirmation configurations for FIGS. 6 to 8, the configuration of the straps has been specifically designed to work in conjunction with the support to offer a high degrees of posture support by both stabilizing the upper back, shoulders and lower neck simultaneously. The postero-superior part of the neck support has been designed to guide the brace during neck extension with wearing a protective helmet (hard-hat) while the anterior surface of the brace follows the normal lordotic curve of the neck. The posterior surface of the neck support also follows a helical strap attachment that accommodates wearing a jacket over the support. The inferior surface at the midline of the support has been technically designed to rest, not on the neck, but on the upper back contour in order to provide further comfort and support.

The above-described embodiments of the present invention are intended to be examples only. Alterations, modifications and variations may be effected to the particular embodiments by those of skill in the art without departing from the scope of the invention, which is defined solely by the claims appended hereto.

What is claimed is:

1. A neck support comprising:
    a top portion for receiving user's head;
    a bottom portion having a pair of wings for resting on shoulders of said user;
    a middle portion, connecting said top potion to said bottom portion;
    said top and middle portions are made of a compressive mould material having memory characteristics;
    wherein said bottom portion further comprises a central notch for resting on a user's neck, said notch extending substantially perpendicular to a longitudinal axis of said bottom portion.

2. The neck support device of claim 1 wherein said compressive mould material is a gel-form polyurethane.

3. The neck support of claim 1 wherein said top portion comprises a pocket for receiving a base of a user's head.

4. The neck support of claim 1 further comprising:
    a harness, attached to said bottom portion;
    wherein said harness is worn by said user to maintain the position of the neck support when in use.

5. The neck support of claim 4 wherein said harness comprises a set of straps.

* * * * *